United States Patent [19]
Suciu-Foca et al.

[11] Patent Number: 4,816,404
[45] Date of Patent: Mar. 28, 1989

[54] LATE DIFFERENTIATION ANTIGENS ASSOCIATED WITH HELPER T LYMPHOCYTE FUNCTION

[75] Inventors: Nicole Suciu-Foca, Cliffside Park, N.J.; Donald W. King, Chicago, Ill.

[73] Assignee: The Trustees of Columbia University in the City of New York, New York, N.Y.

[21] Appl. No.: 830,697

[22] Filed: Feb. 18, 1986

Related U.S. Application Data

[63] Continuation-in-part of Ser. No. 752,397, Jul. 5, 1985.

[51] Int. Cl.$^4$ .................. C12N 5/00; C07K 15/04
[52] U.S. Cl. ........................... 435/240.27; 530/387; 424/85.8; 435/68; 435/172.2; 935/104; 935/110
[58] Field of Search ............... 435/240, 241, 68, 70, 435/172.2, 240.27; 935/104, 110; 530/387; 424/85

[56] References Cited

PUBLICATIONS

Andreesen, R. et al, Blood, 63(6):1299–1302 (6–1984).
Feldmann, M. et al, *IR Genes*, Pierce, C. W. ed., Humana Press, Clifton, N.J. (1983), pp. 589–597 cited in Chemical Abstract 99:174084q.
Pilkington, G. R. et al, Pathology 16(4):447–454 (1984) cited in Biosis Abstract 85:271016.
Suciu-Foca et al., *Nature, vol. 318, pp. 465–467, Dec. 5, 1985.*
Suciu-Foca et al., *Transplantation Proceedings*, vol. XVII, No. 1, pp. 716–719, Feb. 1985.
Reed et al., *Transplantation Proceedings*, vol. XVII, No. 1, pp. 735–738, Feb. 1985.

*Primary Examiner*—Margaret Moskowitz
*Attorney, Agent, or Firm*—John P. White

[57] ABSTRACT

Late differentiation antigens ($LDA_1$ and $LDA_2$) expressed by activated helper cells are described. $LDA_1$ and $LDA_2$ are membrane proteins recognized by monoclonal antibodies produced by immunizing mice with alloreactive human T cell clones with helper function. $LDA_1$ and $LDA_2$ are expressed by helper T cells. $LDA_1$ monoclonal antibody and $LDA_2$ monoclonal antibody block T cell enhancement of B cell immunoglobulin production. Thus, $LDA_1$ and $LDA_2$ are associated with helper T cell effector function. Methods of diagnosis and therepy based upon $LDA_1$ and $LDA_2$ are also described.

2 Claims, 8 Drawing Sheets

LATE DIFFERENTIATION ANTIGENS ASSOCIATED WITH HELPER T LYMPHOCYTE FUNCTION

The invention described herein was made with the government support under Grant 1 P01 AG 02307-01 from the National Institute of Health, U.S. Department of Health and Human Services, and Contract NO1-AI-82552 with the National Institute of Allergies and Infectious Diseases, U.S. Department of Health and Human Services. The U.S. Government has certain rights in this invention.

This application is a continuation-in-part of U.S. Ser. No. 752,397, filed July 5, 1985, pending, the contents of which are hereby incorporated by reference.

BACKGROUND OF THE INVENTION

There are three important subpopulations of T Lymphocytes (T cells): helper T cells, which interact with B cells to amplify production of antibody; effector T cells, which carry out the direct cell-killing function of T cells and make certain lymphokines (non-antibody products) which are responsible for delayed hypersensitivity; and supressor T cells, which participate in the regulation of both antibody-medicated and cell-mediated immunity.

T cells must be activated before any of these forms of activity are expressed. Usually the activation follows from exposure to antigen, but other less specific factors such a interleukin 2 are also believed to participate in the activation of T cells.

Usually there is a latent period of around a week to 10 days after first exposure to antigen before the T cells develop initial reactivity. Shortly after that the reactivity subsides. Upon a second contact with antigen, T cells show an accelerated memory response with high activity developing within 2-5 days.

The addition of antigen to cultured lymphocytes induces a small proportion of T cells to differentiate into the large rapidly dividing blast cells. T cells can also be transformed by culturing them together with the lymphocytes of individuals of the same species, a so-called mixed lymphocyte culture. Because of extensive polymorphism at HLA loci, the two cell populations are virtually always different antigenically and they stimulate each other to undergo blast transformation. For example, isolated blood lymphocytes from recipient and prospective donor are maintained together for several days in tissue culture. Blast transformation occurs if allogenic cells are present. This process may be referred to as alloactivation. Mixed lymphocyte cultures may be established by treating one set of cells in a manner that prevents blast transformation of that set of cells such as irradiating the cells.

A T lymphocyte will recognize an antigen only if the antigen is properly presented by a presenting cell which in many cases is a macrophage. The antigen must be presented juxtaposed to a compatible Ia molecule, a surface molecule coded for by one of the class I transplantation or histocompatibility genes. In man, there are at least two distinct families of Ia molecules encoded by mixed lymphocyte culture genes, HLA-DR and MT or DS. These genes control the formation of the specialized complementary Ia structures on the surface of a presenting cell and the T cells that provide for proper presentation of antigens. T cells may interact with B cells, or other T cells, if the cell possesses complementary Ia structures and if it recognizes the same antigenic determinant or a different determinant on the same antigenic molecule.

During the process of activation, T cells develop new surface antigens, so-called T cell activation antigens. Most of these T cell activation antigens, however, are not T cell specific. For example, the transferrin receptor, the insulin receptor and the 4F2 antigen appear on proliferating cells of many types. Only one T cell activation antigen, Tac (Interleukin-2 receptor), is found only on activated T cells.

The kinetics of antigen appearance on activated T cells has been studied in order to gain some insight into the function of these molecules. Cotner et al. examined the kinetics of appearance of several T cell antigens and found that each exhibited a characteristic and reproducible time of appearance (9). Based upon this, the antigens could be classified as early, intermediate or late appearing antigens.

The relevancy of various cell surface markers to the functional heterogeneity of alloreactive T cell clones has been examined and the rearrangement of the T B-chain gene of the antigen receptor in wild and mutant variants of clones with altered phenotypes and function compared (7). BALB/C mice have been immunized with helper T cell clones to produce two monoclonal antibodies which detect distinct cell surface molecules associated with T cell helper activity and with the production of T replacing factor (8).

The 4F2 antigen, Tac, the 49.9 antigen and the transferrin receptor appear within 24 hours of mitogen stimulation, before the onset of DNA synthesis, and are classified as early antigens. Early appearing antigens may be associated with cell growth. The HLA-DR antigen and the 19.2 antigen (Ia antigen) do not appear until about 72 hours after activation and are classified as late antigens. Expression of the OKT 10 antigen by activated T cells is intermediate.

The molecule or molecules associated with T cell helper function are unknown. Human helper T cells are defined as lymphocytes which express the T4 surface antigen, a T cell specific glycoprotein molecule expressed by cells which recognize and are restricted by major histocompatibility complex class II antigens. This molecule is also found on killer and suppressor lymphocytes suggesting that the T4 molecule is not involved in helper function. Similarly, the T cell antigen receptor does not seem to be involved in any specific T cell function because the gene which encodes the B-chain of the receptor is rearranged and expressed by helper, suppressor and cytotoxic T cells.

SUMMARY OF THE INVENTION

This invention pertains to a late appearing T cell differentiation antigen, designated $LDA_1$, which is expressed by activated human helper T lymphocytes and is associated with the function of a T cell helper/inducer of B lymphocyte immunoglobulin production. The invention also pertains to monoclonal antibody against $LDA_1$ and to methods of therapy and diagnosis utilizing the antigen and antibody against it. The $LDA_1$ monoclonal antibody is produced by a hybridoma cell line designated CU-B103H8. This hybridoma cell line has been deposited under ATCC No. HB89020. The invention also pertains to a method of assessing helper T cell function comprising determining the level of $LDA_1$ expression on the surface of T cells. The invention also pertains to a method of suppressing the immune response in an individual, comprising administering an immunosuppressing amount of $LDA_1$ monoclonal antibody. The invention also pertains to a method of enhancing immune response in an individual comprising administering to the individual an effective amount of isolated $LDA_1$.

$LDA_1$ was identified as a membrane protein recognized by a murine monoclonal antibody produced in a mouse immunized with an alloreactive human helper T cell clone. $LDA_1$ is expressed mainly by T cells bearing the $T_4$ surface antigen i.e. by helper T cells. Studies of the kinetics of $LDA_1$ is expressed by T cells optimally at about 9 days after in vitro activation with plant mitogens (e.g. PHA) and about 9 days after alloactivation in one-way mixed lymphocyte culture with allogeneic peripheral blood mononuclear cells. The antigen is not expressed by unactivated (resting) peripheral blood T or B lymphocytes or by Epstein-Barr virus transformed B lymphoblastoid cell lines.

$LDA_1$ is a surface protein comprised of two subunits of approximate molecular weight 100KD and 150KD. Utilizing $LDA_1$ monoclonal antibody. The antigen was immunoprecipitated by reacting the antibody with the immunizing helper T cell clone. The immunoprecipitated antigen was run on sodium dodecylsulfate polyacrylamide gel electrophoresis. Two bands were identified as having the designated molecular weight.

$LDA_1$ monoclonal antibody blocks helper T cell enhancement of B cell immunoglobulin production. In a Pokeweed mitogen driven system, T cells induce immunoglobulin production by B cells. $LDA_1$ monoclonal antibody inhibits T cell inducement of Ig production in this system. IgG and particularly IgM production can be significantly reduced by antibody.

The discovery of $LDA_1$ provides new procedures of diagnosis and therapy. $LDA_1$ provides new procedures of diagnosis and therapy. $LDA_1$ is expressed by activated helper T cells and serves as a marker of these cell types. Assessment of $LDA_1$ expression can be an indicator of T cell hypoactivity or hyperactivity. The isolated antigen may have therapeutic utility as a helper factor for amplifying immunoglobulin production. Anti-$LDA_1$ blocks the helper activity of T cells and can be used to supress the immune response. The antibody may be valuable in therapy of autoimmune disease and as an agent for inhibition of allograft rejection.

This invention also pertains to a late appearing T cell differentiation antigen, designated $LDA_2$, which is expressed by activated human helper T lymphocytes and is associated with the function of a T cell helper/inducer of B lymphocyte immunoglobulin production. The invention also pertains to monoclonal antibody against $LDA_2$ and to methods of therapy and diagnosis utilizing the antigen and antibody against it. The $LDA_2$ monoclonal antibody is produced by a hydridoma cell line designated CU-2974B9. This hybridoma cell line has been deposited under ATCC No. HB9019.

The invention also pertains to a method of assessing helper T cell function comprising determining the level of $LDA_2$ expression on the surface of T cells. The invention also pertains to a method of suppressing the immune response in an individual, comprising administering an immunosupressing amount of $LDA_2$ monoclonal antibody. The invention also pertains to a method of enchancing immune response in an individual comprising administering to the individual an effective amount of isolated $LDA_2$.

DETAILED DESCRIPTION OF THE INVENTION

This invention pertains to a late appearing T cell differentiation antigen, designated $LDA_1$, which is expressed by activated human helper T lymphocytes and is associated with the function of a T cell helper/inducer of B lymphocyte immunoglobulin production. The invention also pertains to monoclonal antibody against $LDA_1$ and to methods of therapy and diagnosis utilizing the antigen and antibody against it.

The $LDA_1$ monoclonal antibody is produced by a hybridoma cell line designated CU-B103H8. This hybridoma cell line has been deposited with the American Type Culture Collection in Rockville, Md., U.S.A. 20852 under ATCC No. HB9020. This deposit was made pursuant to the provisions of the Budapest Treaty on the International Recognition of the Deposit Microorganisms.

The invention also pertains to a method of assessing helper T cell function comprising determining the level of $LDA_1$ expression on the surface of T cells. The method comprises the steps of isolating peripheral blood mononuclear cells, reacting the cells with $LDA_1$ monoclonal antibody, and determining the amount of antibody bound to the surface of the cells. The invention also pertains to a method of suppressing the immune response in an individual, comprising administering an immunosupressing amount of $LDA_1$ monoclonal antibody. The invention also pertains to a method of enhancing immune response in an individual comprising administering to the individual an effective amount of isolated $LDA_1$.

$LDA_1$ is a T cell surface antigen which is characterized as follows:

a. $LDA_1$ is expressed by activated helper T cells, but not by resting peripheral T or B lymphocytes;

b. $LDA_1$ expression is expressed optimally by T cells nine days after stimulation in primarily mixed lymphocyte culture;

C. $LDA_1$ expression is dependent upon DNA and protein synthesis by activated T cells;

d. $LDA_1$ monoclonal antibody inhibits accelerated specific memory response to HLA-D/DR antigens when added to primary mixed lymphocyte cultures within the first 24 hours or primary stimulation; and e. $LDA_1$ monoclonal antibody blocks helper T cell enhancement of immunoglobulin production of mitogen stimulated B cells.

The late expression of $LDA_1$ and the capability of $LDA_1$ monoclonal antibody to block T cell helper function indicate that $LDA_1$ is a molecule associated with the effector function of helper T cells. The antigen may also be involved in specific memory responses.

As a molecule associated with helper T cell function, and perhaps directly responsible for it, the measurement of $LDA_1$ expression has diagnostic import. Because $LDA_1$ is distinctive to activated helper T cells, it is a unique marker for these cells in a population of lymphocytes. Moreover, the level of expression of $LDA_1$ provides a measure of helper T cell helper activity.

This can be important information for evaluation of the immune status of an individual. For instance, in therapy of certain diseases, such as cancer, agents which affect the immunocompetency are often used. Assays $LDA_1$ expression may allow physicians to monitor the immune status of the patient and to adjust therapy to minimize the risk of opportunistic infection, often a threat to immunocompromised patients.

The level of expression of $LDA_1$ can also be used in diagnosis of infection or of diseases related to T cell hypoactivity of hyperactivity. During bacterial or viral infection, helper T cell activity is generally increased as part of the immune response to the invading organisms. Increased $LDA_1$ expression associated with enhanced T cell activity can provide an indication of infection. In addition, certain autoimmune diseases are believed to be related to an hyperactive immune system. $LDA_1$ expression can provide an assessment of this hyperactivity.

Assays for $LDA_1$ expression can be conventional immunochemical assays for cell surface antigens. $LDA_1$ monoclonal antibody is employed. Peripheral blood mononuclear cells can be isolated from a patient and incubated with $LDA_1$ monoclonal antibody under conditions which allow the antibody to bind the surface antigen. Antibody bound to the cell surface provides a measure of $LDA_1$ expression. Binding of the antibody to cells can be evaluated by employing an $LDA_1$ monoclonal antibody labeled with a radioactive, fluorescent or other compound which emits a detectable signal. Alternatively, a labeled second antibody against the $LDA_1$ monoclonal antibody may be used. For example, if the $LDA_1$ monoclonal antibody is murine in origin, an antimurine Ig antibody can be the second antibody. The second antibody is incubated with the cells after the $LDA_1$ monoclonal antibody and the cells are then evaluated for bound label.

$LDA_1$ may be a "helper factor" which mediates helper function. Thus, $LDA_1$ in soluble form may be a useful agent for modulating the immune response. For example, in immunodeficient persons, $LDA_1$ may be useful for restoring immunocompetency. In other situations where an enhanced immunity is desirable $LDA_1$ may be administered. For these purposes, $LDA_1$ can be administered in purified form in immunoenhancing amounts. Generally, $LDA_1$ would be given intravenously in a physiologically acceptable vehicle.

$LDA_1$ monoclonal antibody which, blocks the helper function of T cells, may also have therapeutic value. The antibody can be used to generally suppress immune response. In certain autoimmune diseases related to T cell hyperactivity, $LDA_1$ monoclonal antibody may be effective in treatment. Additionally, the antibody may be useful in suppressing graft-versus-host reactions.

$LDA_1$ monoclonal antibody can be produced in several ways. Polyclonal antibodies can be produced by immunizing animals with isolated $LDA_1$ by conventional techniques to produce polyclonal $LDA_1$ monoclonal antibody antisera.

$LDA_1$ monoclonal antibodies are produced by antibody-producing cell lines. $LDA_1$ monoclonal antibody producing cell lines may be hybridoma cell lines commonly known as hyridomas. The hybrid cells are formed from the fusion of an $LDA_1$ monoclonal antibody-producing cell and in immortalizing cell line, that is, a cell line which imparts along term tissue culture stability on the hybrid cell. In the formation of the hybrid cell lines, the first fusion partner, the $LDA_1$ monoclonal antibody-producing cell, may be a spleen cell of an animal immunized against $LDA_1$. Alternatively, the $LDA_1$ monoclonal antibody-producing cell may be an $LDA_1$ monoclonal antibody-generating B lymphocyte obtained from the spleen, peripheral blood, lymph nodes or other tissue. The second fusion partner, the immortal cell, may be a lymphoblastoid cell or a plasmacytoma cell such as a myeloma cell, itself an antibody-producing cell but also malignant.

Murine hybridomas which produce $LDA_1$ monoclonal antibodies are formed by the fusion of mouse myeloma cells and spleen cells from mice immunized against $LDA_1$. To immunize the mice, a variety of different immunization protocols may be followed. For instance mice may receive primary and boosting immunizations $LDA_1$. The fusions are accomplished by standard procedure (10), (11).

The hybridomas are then screened for production of antibody reactive with $LDA_1$. Those which secrete reactive antibodies are cloned.

Another way of forming the $LDA_1$ monoclonal antibody cell line is by transformation of antibody-producing cells. For example, an $LDA_1$ monoclonal antibody-producing B lymphocyte obtained from a human animal immunized against $LDA_1$, may be infected and transformed with a virus such as the Epstein-Barr virus in the case of human B lymphocytes to give an immortal $LDA_1$ monoclonal antibody-producing cell. See e.g., (12). Instead of the infection with Epstein-Barr virus, the B lymphocyte may be transformed by a transforming gene or transforming gene product.

The $LDA_1$ monoclonal antibodies can be produced in large quantities by injecting $LDA_1$ monoclonal antibody-producing hybridomas into the peritoneal cavity of mice and, after an appropriate time, harvesting the ascites fluid which contains very high titer of homogenous antibody and isolating the $LDA_1$ monoclonal antibodies therefrom. Xenogeneic hybridomas should be injected into irradiated or athymic nude mice. Alternatively, the antibodies may be produced by culturing $LDA_1$ monoclonal antibody-producing cells in vitro and isolating secreted $LDA_1$ monoclonal antibodies from the cell culture medium.

Isolated $LDA_1$ can be produced by cloning and expressing the $LDA_1$ gene. The gene encoding $LDA_1$ can be identified and isolated by at least two techniques, the "cDNA" approach and the "genomic DNA" approach. For the "cDNA" approach, $LDA_1$ can be immunoprecipitated with $LDA_1$ monoclonal antibody. Immunoprecipitated $LDA_1$ can be isolated and partially sequenced. From the protein sequence information, the possible nucleotide sequences of the $LDA_1$ gene can be predicted. DNA probes can be synthesized for all possibilities and used to screen a "cDNA" library of genes from activated T cells to identify clones carrying the $LDA_1$ gene or segments thereof. The library is constructed by synthesizing "cDNA" from mRNA of activated T cells bearing $LDA_1$ and inserting the "cDNA" into appropriate host cells. The gene can be isolated from the identified host and sequenced.

A second approach is the "genomic" approach. The DNA of T cells which express $LDA_1$ is isolated and fragmented. The fragmented DNA is used to transfect a non-human recipient cell line such as mouse fibroblast L cells which can express a foreign membrane protein on their membrane. The transfected clones are screened for expression of $LDA_1$ monoclonal antibody. In the transfection procedure the recipient cell takes up a certain fraction of human DNA. In order to arrive at a clonal cell line which has essentially only the DNA of $LDA_1$ gene, the recipient cells expressing $LDA_1$ can be isolated and used to transfect a second recipient cell. The process can be repeated to segregate the $LDA_1$ gene in a cell. The gene can be identified with human Alu sequence probes.

Once identified, the gene can be cloned and expressed in various host cell systems to provide ample quantities of $LDA_1$ as a soluble antigen for therapeutic and diagnostic uses. Conventional techniques and host/vectors systems can be employed.

This invention also pertains to a late appearing T cell differentiation antigen, designated $LDA_2$, which is expressed by activated human helper T lymphocytes and is associated with the function of a T cell helper/inducer of B lymphocyte immunoglobulin production. The invention also pertains to monoclonal antibody against $LDA_2$ and to methods of therapy and diagnosis utilizing the antigen and antibody against it.

The $LDA_2$ monoclonal antibody is produced by a hybridoma cell line designated CU-2974B9. This hybridoma cell line has been deposited with the American Type Culture Collection in Rockville, Md., U.S.A. 20852 under ATCC No. HB9019. This deposit was made pursuant to the provisions of the Budapest Treaty on the International Recognition of the Deposit Microorganisms.

The invention also pertains to a method of assessing helper T cell function comprising determining the level of $LDA_2$ expression on the surface of T cells. The method comprises the steps of isolating peripheral blood mononuclear cells, reacting the cells with $LDA_2$ monoclonal antibody, and determining the amount of antibody bound to the surface of the cells. The invention also pertains to a method of suppressing the immune response in an individual, comprising administering an immunosupressing amount of $LDA_2$ monoclonal antibody. The invention also pertains to a method of enhancing immune response in an individual comprising administering to the individual an effective amount of isolated $LDA_2$.

$LDA_2$ late differentiation antigen, present on activated T cells but not resting lymphocytes, is associated with the capacity of primed T cells to produce and deliver helper functions which stimulate differentiation of activated B cells into antibody-producing cells. In the presence of $LDA_2$ monoclonal antibody, T cells stimulated in cultures with allogeneic Ia, soluble antigens (tetanus toxoic, PPD, etc.) or with plant mitogens do not produce T Replacing Factor and do not activate B lymphocytes to produce IgG or IgM antibodies. The molecules recognized by the $LDA_2$ monoclonal antibody are 170 and 190 KD membrane protein, as determined by SDS-PAGE analysis of $^{125}I$ labeled membrane extracts from primed T lymphocytes.

Cytofluorometric investigations of $LDA_2$ expression of mononuclear cells from the peripheral blood of healthy individuals yielded completely negative results. Peripheral blood mononuclear cells from dialysis and transplant patients, monitored for the expression of these antigens displayed $LDA_2$ on T lymphoblasts in a pattern consistent with immune activation. Dialysis patients exhibited $60+10\%$ $LDA_2$ positive cells within 3-7 days following transfusion. Transplanted patients (kidney and heart) exhibited $LDA_2$ on more than 30% of peripheral blood mononuclear cells during quiescence, but the percent positive cells increased to 75% during rejections or when immunosuppression was decreased because of other clinical complications.

Isolated $LDA_2$ can be produced by cloning and expressing the $LDA_2$ gene. The gene encoding $LDA_2$ can be identified and isolated by at least two techniques, the "cDNA" approach and the "genomic DNA" approach. For the "cDNA" approach, $LDA_2$ can be immunoprecipitated with $LDA_2$ monoclonal antibody. Immunoprecipitated $LDA_2$ can be isolated and partially sequenced. From the protein sequence information, the possible nucleotide sequences of the $LDA_2$ gene can be predicted. DNA probes can by synthesized for all possibilities and used to screen a "cDNA" from mRNA of activated T cells bearing $LDA_2$ and inserting the "cDNA" into appropriate host cells. The gene can be isolated from the identified host and sequenced.

A second approach is the "genomic" approach. The DNA of T cells which express $LDA_2$ is isolated and fragmented. The fragmented DNA is used to transfect a non-human recipient cell line such as mouse fibroblast L cells which can express a foreign membrane protein on their membrane. The transfected clones are screened for expression of $LDA_2$ with $LDA_2$ monoclonal antibody. In the transfection procedure the recipient cell takes up a certain fraction of human DNA. In order to arrive at a clonal cell line which has essentially only the DNA of $LDA_2$ gene, the recipient cells expressing $LDA_2$ can be isolated and used to transfect a second recipient cell. The process can be repeated to segregate the $LDA_2$ gene in a cell. The gene can be then identified with human Alu sequence probes.

Once identified, the gene can be cloned and expressed in various host cell systems to provide ample quantities of $LDA_2$ as a soluble antigen for therapeutic and diagnostic uses. Conventional techniques and host/vectors systems can be employed.

The invention is illustrated further by the following Exemplification:

EXAMPLES

Example 1

Production of LDA$_1$ monoclonal antibody and Generation and Culture of human T cell clones Peripheral blood mononuclear cells from individual M.W. (HLA-DR3,7) were primed in a 6-day mixed lymphocyte culture against an equal number of irradiated lymphocytes from an HLA-DR half-identical allostimulator, individual R.C. (HLA-DR1,3). Lymphoblasts were isolated by differential centrifugation on a 55% isotonic percoll suspension (1.072 g/ml) followed by centrifugation through a 30% percoil suspension for removal of dead cell debris. The purified lymphoblasts were diluted to 33 cells/ml in RPMI 1640 medium supplemented with 20% T cell growth factor (Cellular Products, Buffalo, N.Y.), 15% heat-inactivated fetal calf serum, glutamine and antibiotics. Ten microliter aliquots were plated in sterile 60-well microtest II trays. To each well was added irradiated (4000 rad) B lymphoblasts (10,000 cells/well) obtained by Epstein-Barr virus transformation of B cells from R.C. The wells that showed positive growth were transferred successively, at 7-day intervals, to 96- and 24- well trays and then to 25 cm$^2$ tissue culture flasks containing the appropriate concentration of T cell growth factor and feeders. Selected clones were expanded by weekly restimulation with irradiated lymphoblastoid cells of stimulator origin. Clones were tested for mixed lymphocyte culture reactivity against the original stimulator in a 72-h blastogenesis assay, using controls DW1/DR1-positive and DW1/DR1-negative stimulting cells (13). Clone 19 was selected as an immunogen for preparation of T cell receptor-specific antibodies, since it was exquisitely specific for DW1/DR1+-positive targets (r=0.86) C.

Immunization and Production of LDA$_1$ Monoclonal Antibodies

BALB/c mice were immunized three times. For each injection we used 7×10$^6$ cloned T cells from the anti-DR1 clone 19 whose phenotype was OKT3+, OKT4$^4$, OKT6−, OKT8−, OKT11+, Ia+. The last injection was given 2 days prior to fusion.

Splenocytes from immunce BALB/c mice were fused with NS-1 plasmocytoma cells using the polyethyelene glycol fusion procedure (14). Of 1900 wells seeded at 1×10$^4$ cells/well, 1700 wells showed hybridoma growth within 2 weeks. Culture supernatants were tested for antibody activity against human monocytes, T and B lymphocytes of complement-dependent lymphocytoxicity using goat antimouse Ig immunoglobulin for detection of noncytotoxic antibodies. Eight hundred and twenty hybridomas showing no reactivity with peripheral blood leukocytes were further tested by cytofluoremetry on T lymphoblasts (mixed lymphocyte culture and phytohemaglutinin-activated blasts), Epstein-Barr virus-transformed B lymphoblastoid cells (including lines autologous to the T cell clone and to its stimulator), T cell leukemias, and T cell clones.

Selected hybridomas which seemed to react with cloned T cells 19 but not with other targets were cloned by limiting dilutions and injected into pristane-primed BALB/c mice. The resulting ascitic fluid was used as a source of antibody.

Cytofluorometric determination of the reactivity of LDA$_1$ monoclonal antibody with T cells LDA$_1$ monoclonal antibodies were tested for binding to cell-surface antigens by indirect imunofluorescense. One hundred thousand cells were incubated with 100 microliters hybridoma supernatant for 30 min. at 4° C. in the presence of 10 microliters human serum. The cells were washed three times with phosphate-buffered saline containing 2.5% fetal calf serum and 0.05% NaN$_3$, and then incubated with 100 microliters of a 1:40 dilution of FITC-conjugated goat antimouse Ig immunoglobulin (Meloy, Springfield, Va.) for 30 min at 4° C. in the presence of human serum. Before analysis of binding on an Ortho Spectrum III Cytofluorometer, the cells were washed three times with phosphate buffer saline containing 2.5% fetal calf serum and 0.05% NaN$_3$. For direct immunofluorescence, immunoglobulin was purified from the ascitic fluid of mice injected with the relevant hybridoma and conjugated with FITC by standard procedures.

On initial screening, 820 of the 1700 hybridomas failed to react with monocytes and T and B lymphocytes from an HLA reference panel of 50 individuals. As shown in Table 1, one of these 820 antibody-secreting hybridomas reacted with the immunizing B-lymphoblastoid lines or unrelated cloned T cells. Following sequential subcloning, LDA$_1$ monoclonal antibody was selected for further testing on 65 OKT4+ and 15 cloned T cells derived from mixed lymphocyte culture blasts of M.W. (HLA-DR3,7) primed to R.C. (HLA-DR1,3). LDA$_1$ monoclonal antibody reacted with 10 of 65 OKT4+ cloned T cells (including cloned T cells 19), but with no OKT8+ cloned T cells. Six of these LDA$_1$ monoclonal antibody positive cloned T cells were twin clones of cloned T cells 19. The remaining three derived from another mixed lymphocyte culture in which M.W. was primed to R.C. All of the LDA$_1$ monoclonal antibody positive cloned T cells were anti-DRI reactive, as determined by blastogenic responses to selected stimulators. There were, however, other cloned T cells which, although anti-DRI reactive, showed no binding LDA$_1$ monoclonal antibody.

EXAMPLE 2

Identification and Characterization of LDA$_1$

The expression of LDA$_1$ on T lymphocytes stimulated in vitro with plant mitogens or with irradiated allogeneic peripheral blood mononuclear cells was monitored by indirect immunofluorescence on an Ortho Spectrum III Cytofluorometer as previously described (2).

Peripheral blood mononuclear cells (10$^6$ cell/ml) were incubated at 37° C. in a humdified 5% CO$_2$ atmosphere in RPMI 1640 medium supplemented with gluatamine, antibiotics and 15% autologous plasma.

TABLE 1

| | Cytofluorometric determination of reactivity of LDA$_1$ monoclonal antibody with human lymphocytes | | | | | | | | |
|---|---|---|---|---|---|---|---|---|---|
| | Anti-Dr$_1$ cloned T cells from M.W. | | Unrelated allo-reactive cloned T cells | Mixed lymphocyte culture blasts | PHA plant mitogen blasts | T-cells leukemias | Epstein-Barr virus B-cells lines | Normal Peripheral blood lymphocytes | |
| Targets | OKT4$^+$ | OKT8$^-$ | | | | | | T cells | B cells |
| No. tested | 65 | 15 | 16 | 19 | 15 | 5 | 20 | 50 | 50 |
| No. reacting with LDA$_1$ monoclonal antibody | 10 | 0 | 0 | 0 | 0 | 0 | 0 | 0 | 0 | cultures were stimulated with phytohemaglutinin (1 microgram/ml phytohemaglutinin/M Difco), Pokeweed Mitogen (10 microgram/ml Pokeweed Mitogen, Grand Island Biological Co.) or irradiated HLA-D/DR different allogeneic cells (10$^6$ cells/ml). Reactivity with LDA$_1$ monoclonal antibody was assessed daily by indirect immunofluorescence on a Spectrum III Cytofluormeter using fluorescein conjugated goat anti-mouse Ig (Cappel Lab., Cochranville) for staining the cells.

Phytohemaglutinin stimulated T lymphoblasts from 3-day cultures, were layered on a Percoll gradient, washed, resuspended at 10$^6$ cells/ml and further propagated in culture medium containing 20% interleukin-2 (Biotest). (FIG. 1 upper panel)

T lymphoblasts (10$^6$ cell/ml) obtained from 6-day mixed lymphocyte culture by Percoll gradient configuration were resuspended in "conditioned" medium containing 20% interleukin-2 and irradiated (2500r) peripheral blood mononuclear cells (10$^6$ cells/ml) from the original stimulating cell donor. Cultures were propagated by adding fresh conditioned medium every third day and irradiated stimulating cells every seventh day. LDA$_1$ expression was monitored weekly. Histograms show total number of T lymphoblasts (vertical axis) versus green fluorescence intensity (horizontal axis) Reactivity of mixed lymphocyte culture blasts with LDA$_1$ monoclonal antibody following 2 and 3 weeks in culture is shown on the lower left and lower right panel respectively. (FIG. 1 lower panel)

Figure 1A:
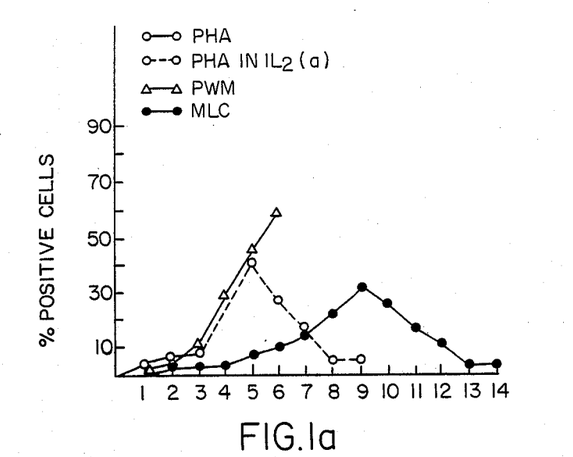
FIG. 1 illustrates the kinetics of expression of $LDA_1$ on in vitro activated T lymphoblasts.
Figure 1B:
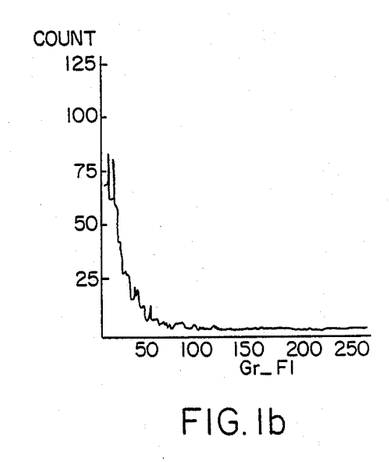
Figure 1C:
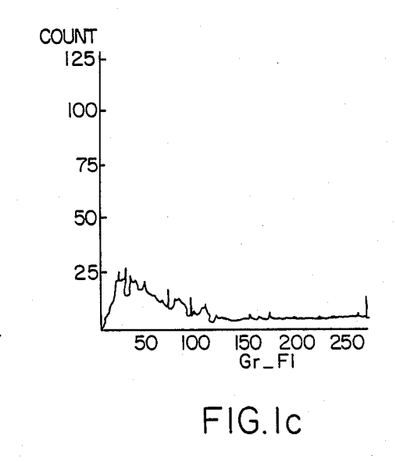

Results obtained with activated T cells from eight different individuals were very similar and are illustrated in FIG. 1. Less than 20% of the PHA plant mitogen activated T lymphoblast express LDA$_1$ within the first 72 hours of incubation. When day-3-PHA plant mitogen-blasts were expanded in medium containing 20% interleukin-2 (Biotest), the fraction of the lymphoblast population on which LDA$_1$ was present increased to 40% by day-2, yet declined steadily thereafter, although the cells continued growing. To determine whether the expression of LDA$_1$ depends on cell proliferation and protein synthesis, day-3-PHA plant mitogen-blasts were incubated at 37° C. for 30 minutes with mitomycin C (25 micrograms/ml, Sigma Chemical Co., St. Louis, MO) or for two hours with emetine-HCL (5×10$^6$M, Sigma Chemical Co.) then washed extensively, cultured in medium with interleukin-2 and monitored by cytofluorometry for cell surface markers. LDA$_1$ induction seems dependent on protein synthesis since pretreatment with emetine, or irreversible inhibitor of protein synthesis at the level of translation or with mitomycin C, a potent inhibitor of DNA synthesis, prevented the proliferative response and expression of LDA$_1$ on cells which stayed viable for 72 hours (15). The LDA$_1$ monoclonal antibody had no effect on the blastogenic response to PHA plant mitogen of T lymphocytes from fresh peripheral blood mononuclear cells.

Cytofluorometric evaluation of LDA$_1$ expression on cells grown in primary mixed lymphocyte culture showed that the percent LDA$_1$ positive T blasts reaches 30 by day-9 and decreases to background levels by day-14 (FIG. 1). The fraction of the population expressing LDA$_1$ was increased, however, to 70% when day-6 HLC-T lymphoblasts were expanded by continuous stimulation with irradiated cells from the sensitizing donor in interleukin-2 supplemented medium (FIG. 1).

To determine whether the percent LDA$_1$ positive cells can be further increased, T cell lines which have been grown for one month in medium containing interleukin-2 and stimulating cell and expressed LDA$_1$ on 70% of the cells, were subjected to sorting experiments by utilizing a fluorescence-activated cell sorter (FACS-I; Becton-Dickinson, Mountain View, CA). Sorted cells were cultured at 37° C. in medium containing interleukin-2 in the presence of an equal number of irradiated peripheral blood mononuclear cells from the stimulating cell donor. Both the positive T lymphoblasts after 48 hours, and 60+15% positive cells 120 hours following sorting. This indicates that LDA$_1$ modulates on the surface of the alloactivated T lymphoblasts by which it is synthesized.

When added at the initiation of primary mixed lymphocyte cultures, the LDA$_1$ monoclonal antibody did not inhibit significantly the primary day-5-blastogenic response which was assessed by the rate of $^3$HTdR incorporation.

Figure 2A:
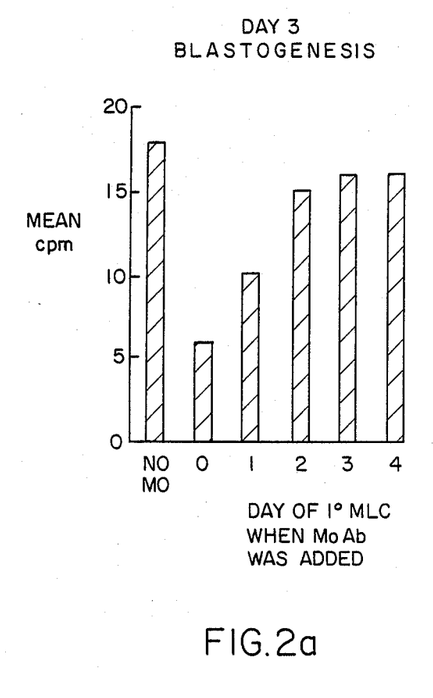
FIG. 2 shows the effect of $LDA_1$ monoclonal antibody on secondary mixed lymphocyte culture responses.
Figure 2B:
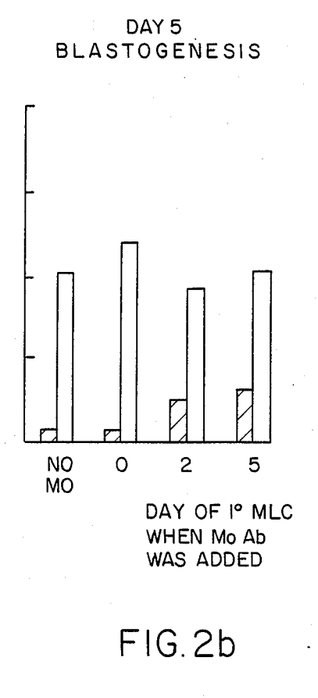

Since the expression of LDA$_1$ is acquired only during late stages of the primary mixed lymphocyte culture response (day-9), the effect of LDA$_1$ monoclonal antibody on secondary mixed lymphocyte culture reactions was investigated. Lymphocytes from a responder with the HLA-DR5, 9 phenotype were primed in mixed lymphocyte culture to HLA-DR5, 7 stimulating cells. Monoclonal antibody anti-LDA$_1$ was added to individual cultures on day 0, 1, 2, 3, 4 or 5. The secondary mixed lymphocyte culture response was tested on day 10 by rechallenging the cultures with stimulating cells. Ten days after the initiation of the primary cultures, cells were collected from each flask, centrifuged on a Ficoll gradient for removal of dead cell debris, adjusted to 5×10$^4$ viable responding cells per microtest well and challenged in triplicate reactions with HLA-DR7 positive or DR7 negative stimulating cells. Secondary cultures were labeled with $^3$H-TdR for 18 hours and harvested on day-3 or on day-5 following restimulation. Results are expressed as mean CPM×10$^3$.

The reaction to specific, HLA-DR7-positive stimulating cells was an accelerated memory response, which culminated on day-3 and declined by day-5. The day-3 response was strongly inhibited when the LDA$_1$ monoclonal antibody was added to the cultures within the first 24 hours of primary stimulation but not when added later (FIG. 2). None of the cultures showed accelerated (day-3) memory responses to HLA-DR7 negative stimulating cells. They displayed, however, primary-type blastogenic responses to such cells on day-5, as expected for polyclonal population of T cells which are capable to recognize any allelic variants of (nonself) HLA-D/DR antigens in primary cultures. This primary anti-DR blastogenic response was not significantly inhibited in cultures grown with $LDA_1$ monoclonal antibody (FIG. 2). It therefore appears that the $LDA_1$ monoclonal antibody inhibits specific memory responses to HLA-D/DR antigens.

Figure 3:
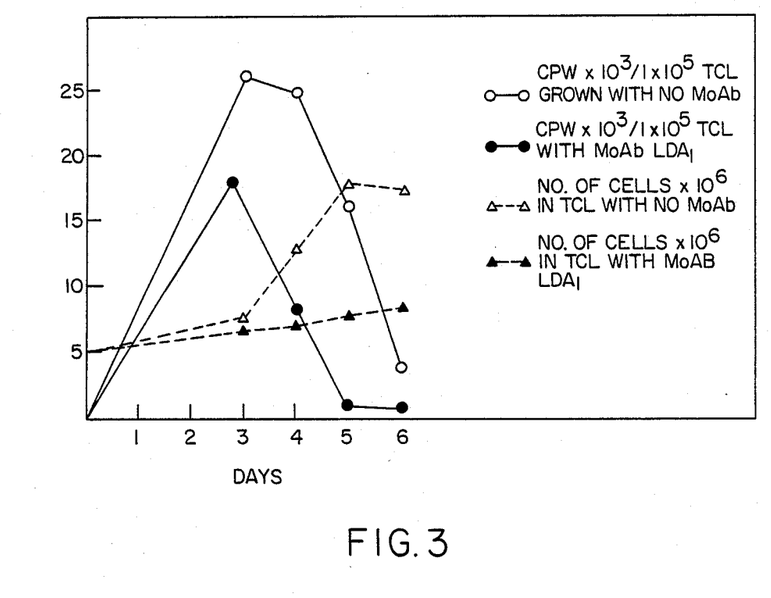
FIG. 3 illustrates the effect of $LDA_1$ monoclonal antibody on rate of growth and $^3HTdR$ incorporation of an alloreactive T cell line (NSF-K) propagated in medium containing interleukin-2 and allogeneic stimulating cells.

This possibility was further explored by determining the effect of the monoclonal antibody on three different anti-HLA-D/DR reactive "bulk" T cell lines and on two T cell clones derived from each of the lines. The NSF-K T cell line was developed by priming PBL from an DR2 homozygous individual to irradiated PBL from a DR3 monozygous stimulator. Day-6 mixed lymphocyte culture blasts were progated for 28 days by weekly stimulation with DR3 positive cells in medium containing 20% interleukin-2. Responding T lymphblasts ($5 \times 10^6$ culture) were tested for reactivity to DR3 positive stimulating cells in the absence or in the presence of $LDA_1$ monoclonal antibody (1:100 final dilution). The number of viable cells and the rate of $^3$H-RdR incorporation was determined on day 3-6. The antibody did not affect the interleukin-2 reactivity of such lines but inhibited strongly the blastogenic response to irradiated peripheral blood mononuclear cells from the stimulating cell donor, as quantitated by the rate of $^3$H-TdR incorporation (FIG. 3).

Since recognition of HLA-D/DR antigens by T lymphocytes is a prerequisite for activating their helper function and since specific anti-Ia responses are inhibited by $LDA_1$ monoclonal antibody, experiments were performed to determine whether this monoclonal antibody also blocks the helper function of resting and allostimulated T lymphocytes.

The helper function of T lymphocytes can be easily quantitated by determining the capacity of T lymphocytes to induce B cell differentiation in a Pokeweed Mitogen driven system (16).

Although $LDA_1$ is expressed on a relatively high proportion of Pokeweed Mitogen stimulated T lymphoblasts (FIG. 1), the $LDA_1$ monoclonal antibody has no consistent inhibitory effect on blastogenic responses induced by Pokeweed Mitogen. This antibody blocks, however, the capacity of helper T cells to enhance immunoglobulin production by autologous Pokeweed Mitogen stimulated B-cells (Table 2). Thus, the amount of IgG and particularly of IgM in supernatants of cultures containing peripheral blood mononuclear cells stimulated for 6 days with Pokeweed Mitogen in the presence of $LDA_1$ monoclonal antibodies was significantly lower than the amount found in control cultures containing no monoclonal antibodies or two other newly developed monoclonal antibodies which recognized the late T cell differentiation antigens.

Peripheral blood mononuclear cells ($1 \times 10^5$/reaction from 6 different responders) were cultured in round bottom microculture plate at 37° C. in a humidified 5% $CO_2$ atmosphere in RPMI 1640 medium supplemented with 15% heat inactivated fetal calf serum, 200 mM L-glutamine, 25 mM HEPES buffer and 1% penicillin/-streptomycin. Peripheral blood mononuclear cells were added to the cultures at a final concentration of 10 micrograms/ml. Replicate cultures were grown with or without $LDA_1$ monoclonal antibody. The amount of IgG and IgM contained in 50 lamda aliquots of day-6 culture supernatant was quantitated in round-bottom polyvinyl trays (Costar) coated with rabbit anti-human IgG or IgM (Dako Accurate Chemicals). Known amounts of human IgG or IgM in the same medium were tested as standards. Triplicate wells were used for each reaction. Following two hours of incubation, wells were emptied, washed in 1% fetal calf serum in phosphate buffered saline and covered with 50 lambda of a 1:3000 or 1:1000 dilution of Peroxidase Conjugated rabbit anti-human IgG or IgM respectively. Trays were incubated for one hour at room temperature in the dark, then washed five times in 1% fetal calf serum/phosphate buffered saline. Fifty microliters of ABTS (2,2 azino-di) (3 ethylbenzthia zoline sulphonic acid) diluted 1:100 in 0.1M citrate buffer (pH 4.2) containing 0.3% Hydrogen Peroxidase were added to each well. Following 30 minutes of incubation at room temperature in the dark, 50 lambda of a 1% solution of sodium dodecyl sulphate were added to stop the reaction. The absorbance at 405 nanometers was read with an automated photometer (Flow Multiskan).

TABLE 2

| | IgM (ng/ml) in cultures tested | | IgG (ng/ml) in cultures tested | |
|---|---|---|---|---|
| Individual No. | WITHOUT $LDA_1$ monoclonal antibody | WITH $LDA_1$ monoclonal antibody | WITHOUT $LDA_1$ monoclonal antibody | WITH $LDA_1$ monoclonal antibody |
| 1 | 8 | 0 | 50 | 2.5 |
| 2 | 8 | 0 | 50 | 1.5 |
| 3 | 35 | 2 | 60 | 3 |
| 4 | 25 | 0 | 20 | 1 |
| 5 | 35 | 0 | 60 | 3 |
| 6 | 9 | 0 | 200 | 7.5 |

Figure 4:
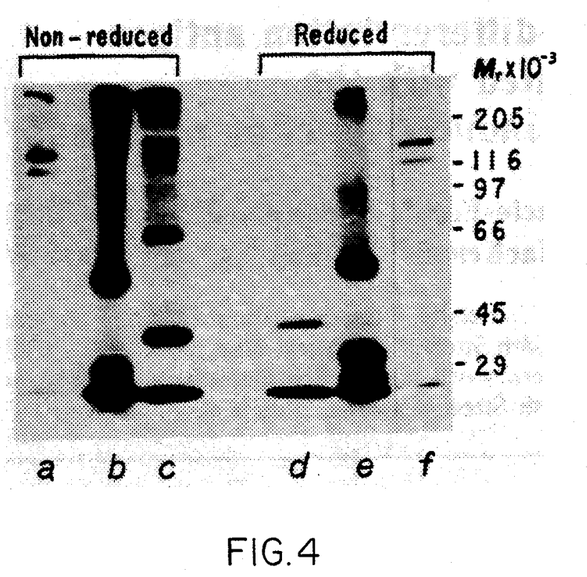
FIG. 4 is a SDS-PAGE analysis of $^{125}I$ labeled membrane proteins of TCC #19 cells.
Figure 5A:
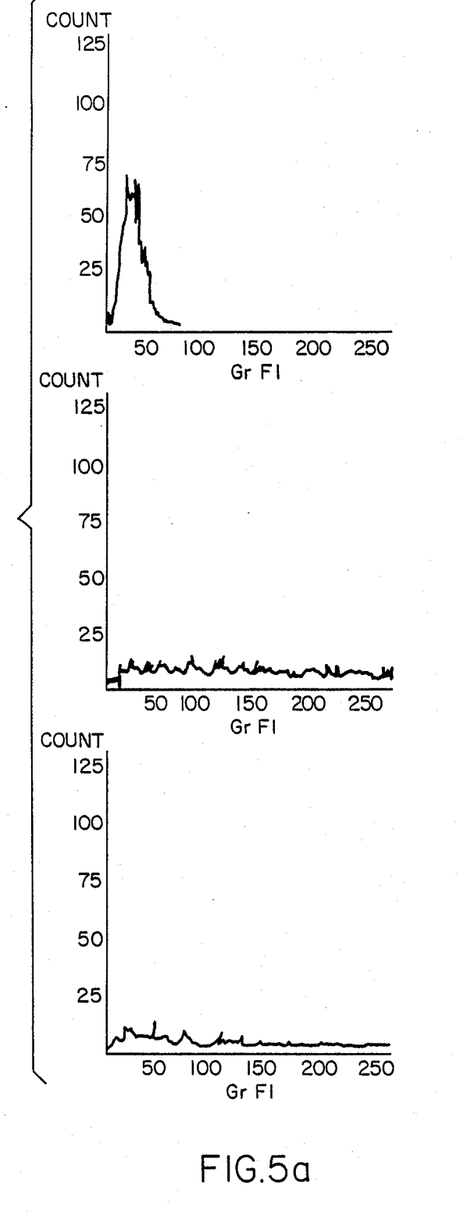
FIG. 5 shows cytofluorographic representation of reactivity of (A) interleukin-2 dependent T cell line; (B) human T cell leukemia virus infected T cell line; (C) lymphoblastoid B cell line; and (D) K-562 (an erythroleukemic cell line) with $LDA_2$ monoclonal antibody (upper panel), anti interleukin-2 receptor (middle panel) and Ia (lower panel).
Figure 5B:
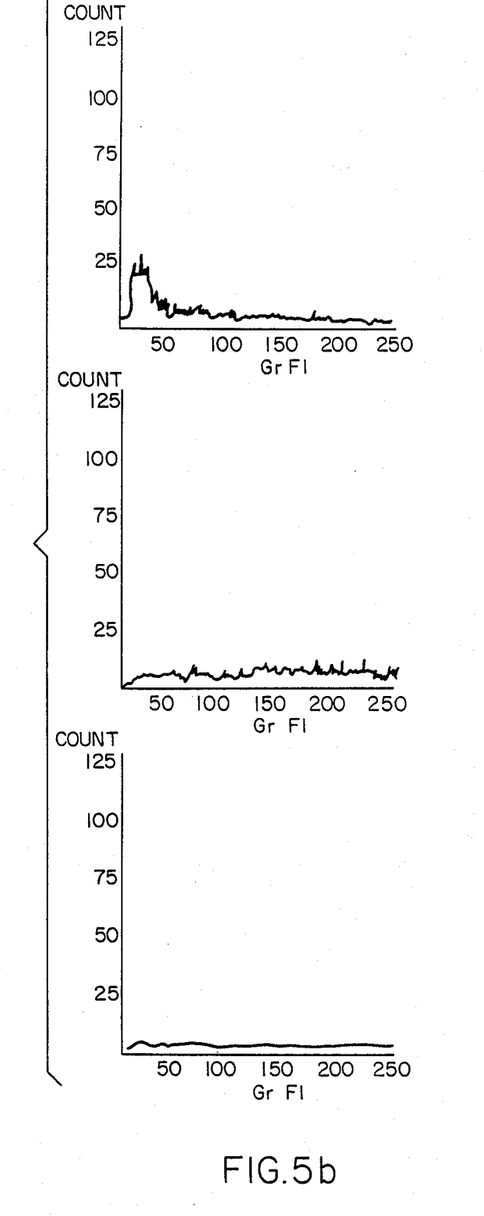
Figure 5C:
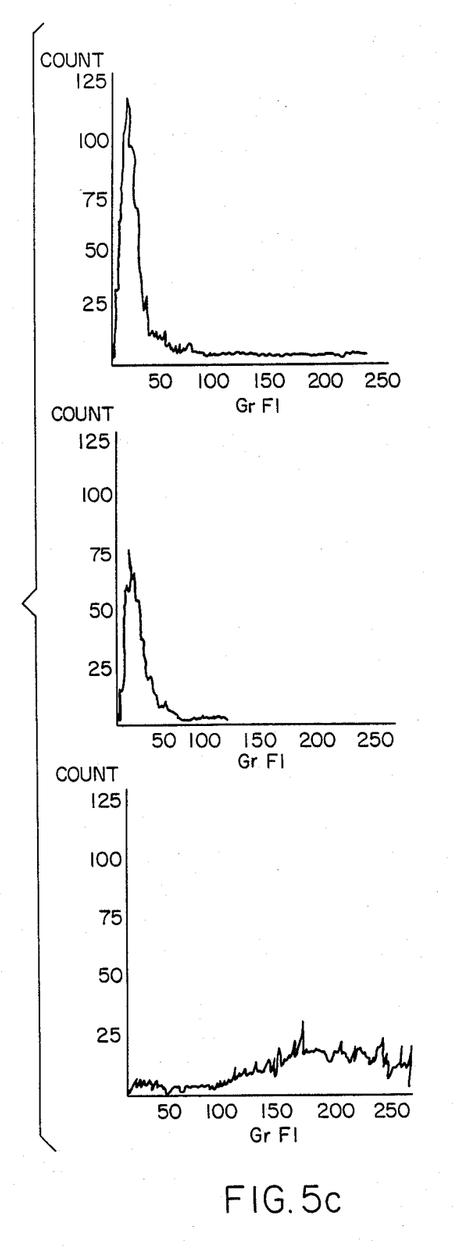
Figure 5D:
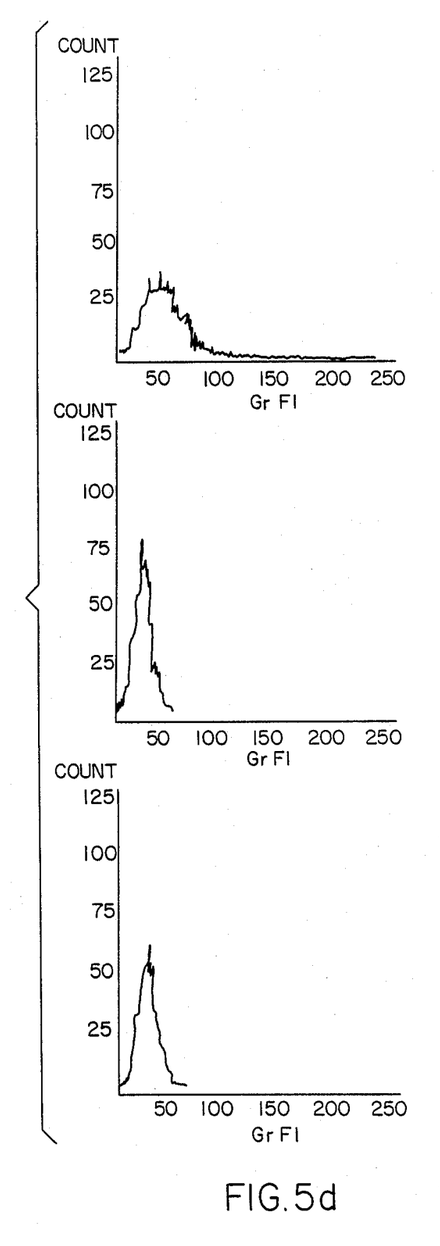

Similar results were obtained when alloreactive T cell clones with high anti-HLAD/DR reactivity and helper function were cultured with stimultor-type B cells, in medium containing Pokeweed Mitogens. Supernatants from cultures to which $LDA_1$ monoclonal antibody was added, contained 80+10% less human immunoglobulin than supernatants from replicate, control cultures without monoclonal antibody. Immunoprecipitation studies of the molecule recognized by the anti-$LDA_1$-monoclonal antibody were performed using $^{125}$I-labeled extracts from the immunizing TCL. $20 \times 10^6$ cells were surface labelled with 1 mCi of $Na^{125}I$ (Amersham) using the lactoperoxidase technique as previously described. Haars et al. Supra. The labelled cells were washed and lysed in 0.5 ml. of 100 mM Tris HCL, pH 7.4/1 mM phenylmethylsulfonyl fluoride/1 mM EDTA/0.5% Triton X-100. Cell lysate was centrifuged at 40,000 xg foir 30 minutes and the supernatent was filtered through a 0.2 micrometer millipore filter. The filtered supernatant was precleared 3 times by sequential 1 hour incubation at 4° C. with protein A-sepharose, rabbit anti-mouse IgG coupled sepharose and an irrelevant monoclonal antibody coupled to sepharose. The precleared cell lysate supernatant was incubated for 4 hours with specific antibody coupled to sepharose 4B, following the immunoprecipitation produced described before. Harris et al. Supra. Immune precipitated were then processed for SDS-PAGE in the presence (reducing condition) of 5% 2-mercaptoethanol using 7.5% polyacrylamide gel ((A,F) $LDA_1$ monoclonal antibody (B,E) A3 monoclonal antibody to a framework determinant of human MHC Class II antigen and (C,D) NAM 1 monoclonal antibody to human $B_2$ microglobulin). Two bands of MW 110 and 150 KD approximately were found under reducing and nonreducing conditions (FIG. 4).

Taken together these data indicate that $LDA_1$ is a late diffetiation cell surface protein expressed by T lymphoblasts with anti-HLA-D/DR reactivity and helper inducer function. This antigen may be encoded by a "helper" function gene or by a T cell receptor gene (possible Fc) involved in antibody production and isotype class switching.

We now describe a late differentiation antigen $LDA_2$ which appears to be associated specifically with the ability of T cells to produce B helper factors.

EXAMPLE 3

Production of $LDA_2$ monoclonal antibody

Monoclonal antibody to $LDA_2$ was produced by immunizing BLB/C mice with three intraperitoneal injections each containing $10^7$ cells from an alloreactive human T cell clone with helper inducer function. Splenocytes from immune mice were fused with the $NS_1$ plasmocytoma as previously described (2).

The $LDA_2$ producing hybridoma was originally selected for subcloning and expansion because it reached with the immunizing T cell clone but not with resting T or B lymphocytes from the same or from different blood donors. The $LDA_2$ monoclonal antibody is of $IgG_1$ subclass as determined by standard immunodiffusion procedure (2). Immunofluorescence studies of antibody binding to cell surface antigens were performed on an Ortho Spectrum III Cytofluorograph (2). The antigen detected by this antibody was found on variable proportions of T lymphoblasts activated in vitro by exposure to plant mitogens (phytohenmaglutinin, ConA and Pokeweed Mitogen), soluble antigens (Purified Protein Derivative and Tetanus Toxoid) or alloantigens, on human T cell leukemia virus-1 infected T cell lines, on Epstein-Barr virus transformed lymphoblastoid cells and on K-562 cells.

FIG. 5 shows cytofluorographic representation of reactivity of (A) interleukin-2 dependent T cell line; (B) human T cell leukemia virus infected T cell line; (C) lymphoblastoid B cell line; and (D) K-562 (an erythroleukemic cell line) with $LDA_2$ monoclonal antibody (upper panel), anti interleukin-2 receptor (middle panel) and Ia (lower panel).

The proportion of T lymphocytes expressing $LDA_2$ following primary in vitro activation increases between day-2 and day-5 and then decreases at various rates. Restimulation of the cultures with antigen and/or interleukin-2 leads to a similar cycle of $LDA_2$ expression in both monoclonal and polyclonal populations of T lymphoblasts. Although priming of T lymphocytes is also accompanied by the expression of other cell surface markers such as the interleukin-2 receptor (Tac) and Ia antigens, there is no association between these determinants and $LDA_2$. Modulation of $LDA_2$ expression occurs sporadically on lymphoblastoid cells, on K-562 line and on human T cell leukemia virus infected cell lines and seems independent on the presence of interleukin-2 and/or antigen in the medium.

EXAMPLE 4

Functional relevance of $LDA_2$ and its effect on blastogenic responses exhibited by peripheral blood mononuclear cells The functional relevance of $LDA_2$ has been evaluated by determining the effect of the $LDA_2$ monoclonal antibody on blastogenic response exhibited by peripheral blood mononuclear cells when exposed to plant mitogens soluble antigens and alloantigens. There was no significant inhibition of the rate of $^3H$-TdR incorporation in phytohemaglutinin stimulated cultures, harvested on day-3 or in mixed lymphocyte culture, harvested on day-6.

This antibody inhibited, however, significantly the day-6 blastogenic response to peripheral blood mononuclear cells, Pokeweed Mitogen, and tetanus toxoid (Table 3). Peripheral blood lymphocytes were prepared by Ficoll Hypaque gradient centrifugation and suspended in RPMI 1640 medium containing 15% fetal calf serum glutamine and antibiotics. Cells were plated at a concentration of $1 \times 10^5$ per well in 96 well Linbro round bottom trays. Pokeweed Mitogen (Gibco, Grand Island Biological, LI) was added at a final dilution of 1:1000 per $10^5$ cells. Tetanus Toxoid was obtained from the Massachusetts Public Health Biological Laboratory and used at a final dilution of 1:400 in complete culture medium. Purified protein derivative of mycobacterium tuberculosis was obtained from Connaught Laboratory, Ontario, Canada and used at a concentration of 3.5 microgram/ml of medium. The effect of monoclonal antibody on the reaction was determined by adding to each culture a final concentration of 1:100 of the respective murine ascites. T cell blastogenesis was determined from the rate of $^3H$-TdR incorporation in cultures with and without $LDA_2$ monoclonal antibody (3). IgG and IgM released in culture supernatant was measured by enzyme-linked immunoabsorbent assay (3). Quantitation of the amount of human IgG and IgM in supernatants of such cultures (3) showed a dramatic decrease of Ig produced in the presence of the antibody as compared to replicate cultures to which no antibody or an irrelevant mouse monoclonal antibody was added (Table 3). Complete inhibition of helper inducer function was also observed when $LDA_2$ monoclonal antibody was added to cultures containing cloned alloreactive T cells and B cells from the stimulating donor.

EXAMPLE 5

Immunoglobulin production by Pokeweed Mitogen stimulated B cells

Figure 6:
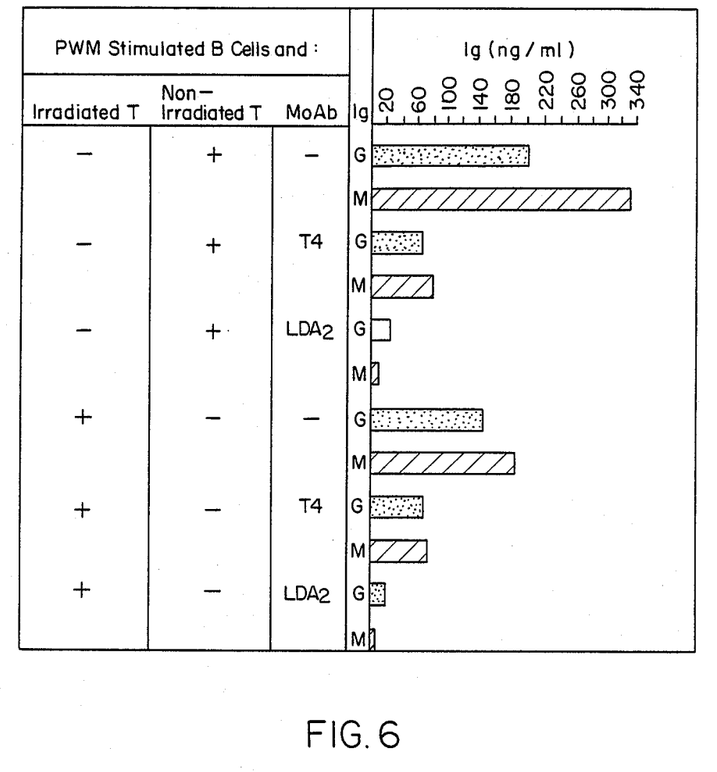
FIG. 6 $LDA_2$ shows monoclonal antibody suppression of the capacity of both irradiated and nonirradiated T cells to activate antibody production by autologous Pokeweed Mitogen stimulated B lymphocytes.
Figure 7:
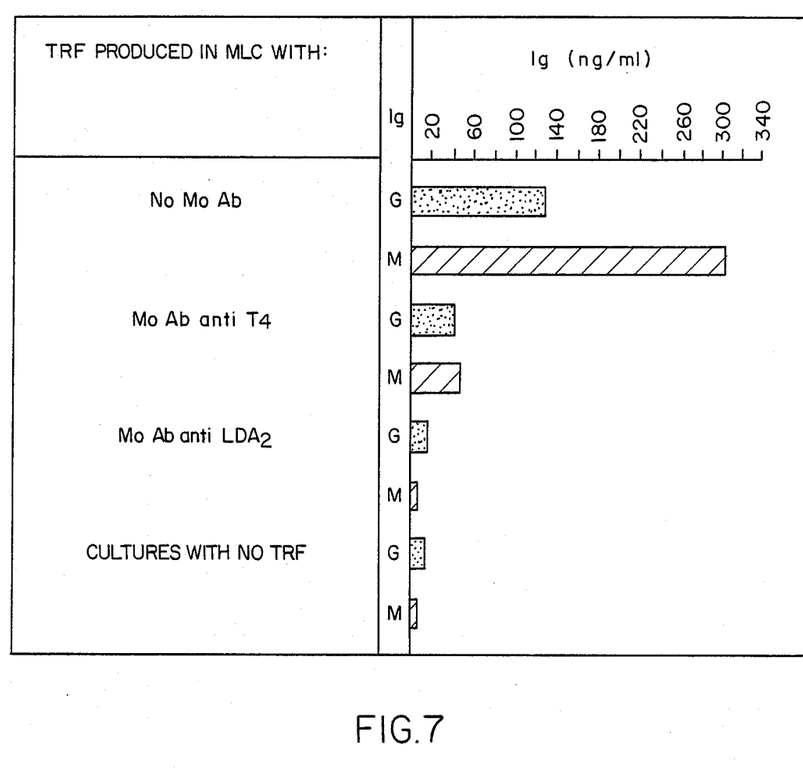
FIG. 7 shows $LDA_2$ monoclonal antibody suppression of T replacing factor activity.

To determine whether the inhibitory effect of this monoclonal antibody is due to inhibition of T cell proliferation or to blockage of T replacing factor production, we tested its effect on the helper activity of nonirradiated (1000r), radioresistant T lymphocytes (4). Purified T and B cell suspensions were separated from fresh peripheral blood mononuclear cells by rosetting the T cell fraction with neuraminidase treated SRBC. B cells suspensions were further depleted of T lumphocytes by treating the non-rosetted fraction with OKT11 monoclonal antibody and fresh rabbit complement. The helper activity of nonirradiated and irradiated (100r) T cells was tested in paralel by incubating $10^4$ T cells with $5 \times 10^4$ autologous B cells in medium containing Pokeweed Mitogen. Murine monoclonal antibody was added to the cultures at a final concentration of 1:100 of the respective ascites. Immunoglobulin production was measured after 6 days of incubation of enzyme-linked immunoabsorbent assay (3). The antibody strongly suppressed the capacity of both irradiated and nonirradiated T cells to activate antibody production by autologous Pokeweed Mitogen stimulated B lymphocytes (FIG. 6). This indicates that the suppressive activity of $LDA_2$ monoclonal antibody on T helper function does not depend on inhibition of T cell proliferation.

natants collected from mixed lymphocyte cell culture grown in the presence of $LDA_2$ monoclonal antibody had minimal T replacing factor activity, i.e. they did not induce Pokeweed Mitogen stimulated B lymphocytes to differentiate and produce antibodies. The anti-$T_4$ monoclonal antibody inhibited T replacing factor production to a much lesser degree. Control supernatants from cultures grown with no monoclonal antibody contained highly potent T replacing factor activity (FIG. 7).

Since $LDA_2$ is also expressed on 30–50% of Epstein-Barr virus-transformed B lymphoblasts, we investigated the possibility tht monoclonal antibody-$LDA_2$ may also affect Ig release from lymphoblastoid cells. There was no inhibition of antibody released into the medium when lymphoblastoid cells were grown in the presence of $LDA_2$ monoclonal antibody.

Immonprecipitation studies of the molecule recognized by $LDA_2$ monoclonal antibody on the surface of T lymphoblasts and K-562 cells were performed using

TABLE 3

Effect of $LDA_2$ monoclonal antibody on the reactivity of human lymphocytes to Pokeweed Mitogen, Tetanus Toxoid, and Purified Protein Derivative

| | Responders | | | | | |
|---|---|---|---|---|---|---|
| | 1 | 2 | 3 | 4 | 5 | 6 |
| % Inhibition of Blastogenic response o: | | | | | | |
| Pokeweed Mitogen | 92 | 23 | 52 | 77 | 80 | 81 |
| Tetanus Toxoid | 95 | 69 | 73 | 79 | 33 | 82 |
| Purified Protein Derivative | 95 | 29 | 74 | 73 | 14 | 97 |
| IgG production in cultures stimulated with: | | | | | | |
| Pokeweed Mitogen | 1950 | 1000 | 2280 | 338 | 896 | 510 |
| Tetanus Toxoid | 390 | 47 | 240 | 176 | 540 | 210 |
| Purified Protein Derivative | 590 | 40 | 540 | 56 | 400 | 180 |
| IgG production in the presence of $LDA_2$ monoclonal antibody: | | | | | | |
| Pokeweed Mitogen | 440 | 6 | 50 | 146 | 40 | 160 |
| Tetanus Toxoid | 0 | 0 | 0 | 12 | 0 | 40 |
| Purified Protein Derivative | 40 | 0 | 10 | 0 | 40 | 20 |
| IgM production in cultures stimulated with: | | | | | | |
| Pokeweed Mitogen | 950 | 1000 | 1950 | 1000 | 1900 | 1650 |
| Tetanus Toxoid | 1350 | 126 | 390 | 489 | 2200 | 250 |
| Purified Protein Derivative | 1010 | 9 | 930 | 33 | 740 | 650 |
| IgM production in the presence of $LDA_2$ monoclonal antibody: | | | | | | |
| Pokeweed Mitogen | 650 | 96 | 70 | 346 | 20 | 470 |
| Tetanus Toxoid | 0 | 10 | 0 | 64 | 30 | 60 |
| Purified Protein Derivative | 0 | 0 | 0 | 1 | 50 | 790 |

Direct proof to this effect has been provided in expeeriments in which T cells were induced to produce B cell growth factors by alloactivation in mixed lymphocyte culture in the presence or in the absence of $LDA_2$ monoclonal antibody. T replacing factor was produced in mixed lymphocyte cell culture containing equal numbers or peripheral blood lymphocytes from six healthy donors. Lymphocytes ($1 \times 10^6$ cells/ml) were grown in RPMI 1640 medium supplemented with glutamine, antibiotics and 15% fetal calf serum for 6 days. The effect of monoclonal antibody on T replacing factor production was determined by adding the antibody to the cultures. Mixed lymphocyte culture supernatants were collected after 6 days and used as T replacing factor. B cell activation in the presence of T replacing factor was determined by culturing $5 \times 10^4$ purified B cells in round bottom 96 well Linbro plates in complete culture medium containing Pokeweed Mitogen (1:200 dilution) and 25% T replacing factor. The amount of human Ig in culture supernatant was measured 6 days later by enzyme-linked immunoabsorbent assay. Super- $^{125}$I extracts. Cells were labeled by the lactoperoxidase method and then extracted with lysis buffer (50 mM Tris/pH 7-6, 0.5% MP-40, 2 mM phenylmethylsulphonylfluoride 20 IU/ml aprotinin). The lysates were precleared with rabbit anti-mouse IgG and anti-melanoma (control) monoclonal antibody coupled sepharose, then reacted with monoclonal $LDA_2$. Immune precipitates were washed and analysed by SDS-PAGE on a 7% gel.

SDS-PAGE analysis of immunoprecipitates from T lymphoblasts showed two major bands of 190 and 170 KD. Only the 190 KD band was found on K-562 cells. Under reducing conditions the 190 KD band migrated in the 92 KD region, possibly due to the dissociation and interchain disulfide bands. Thus, similar to the recently described A-1A5 monoclonal antibody (5), the $LDA_2$ monoclonal antibody recognizes and antigen complex which is only partially expressed on cells other than activated T lymphoblasts. While the A-IA5 antigen is also expressed on resting T cells and is not related to any functional characteristic, LDA$_2$ is absent from non-activated T lymphocytes and is associated with the proodroduction of T replacing factor. In this respect, the LDA$_2$ antigen resembles the LDA$_1$ determinant, which is also associated with T-helper function and yet has a different molecular weight (110 and 150 KD) (3).

It therefore appears that activation of T lymphocytes results in the appearance of functionally relevant membrane antigens which are not present on resting T, although partially expressed on other cells or haematopaetic lineage. The presence of LDA$_2$ on human T cell leukemia virus-I infected T cell lines, known to secrete large amounts of B cell growth factors (6) suggests relatively simple ways for cloning the gene which encodes this molecule.

The LDA$_1$ monoclonal antibody has no effect on the blastogenic response of resting T lymphocytes to stimulation with plant mitogens, soluble antigens or alloantigens. The response to HLA-D/DR antigens of activated T lymphoblasts and of T cell clones is however completely inhibited by this antibody. Furthermore, the LDA$_1$ monoclonal antibody suppresses efficiently the capacity of helper T cell clones to induce B lymphocytes to produce antibody in cultures. LDA$_2$ monoclonal antibody suppresses the proliferative and antibody-inducing helper activity of both resting and primed T lymphocytes. This antibody acts on the radioresistant population of T helper cells by blocking the production of T helper factor. The antibody also binds soluble T replacing factor from culture supernatants. Thus, LDA$_1$ and LDA$_2$ are regulatory molecules involved in T cell helper function. Their late expression on activated T blasts indicates that T helper genes accoording the production of T replacing factor are activated only after antigen triggered proliferation of T cells has been initiated. Since LDA$_1$ monoclonal antibody and LDA$_2$ monoclonal antibody abrogate the helper function of alloreactive T cell clones (Table 4), they may represent important adjuvants for immunosuppressive therapy of transplant recipients.

Equivalents

Those skilled in the art will recognize, or be able to acertain using no more than routine experimentation, many equivalents to the specific embodiments of the invention described herein. Such equivalents are intended to be encompassed by the following claims.

TABLE 4

Effect of LDA$_1$ monoclonal antibody and LDA$_2$ monoclonal antibody on the helper activity of alloreactive T cell clones

| Monoclonal antibody added to the cultures (isotype) | Ig (μg/ml) released in the supernatant of | | |
|---|---|---|---|
| | T cell clone alone | B cell alone | T cell clones + B cells |
| Anti-HLA-A2 (IgG1) | 1 | 30 | 1200 |
| | 10 | 20 | 1400 |
| | 5 | 25 | 800 |
| | 1 | 30 | 1260 |
| LDA$_1$ monoclonal antibody | 0 | 50 | 80 |
| | 0 | 40 | 110 |
| | 0 | 60 | 140 |
| | 0 | 120 | 60 |
| LDA$_2$ monoclonal antibody | 10 | 40 | 10 |
| | 8 | 30 | 20 |
| | 5 | 80 | 100 |
| | 0 | 100 | 110 |
| None | 1 | 60 | 1300 |
| | 5 | 120 | 1500 |
| | 10 | 100 | 800 |
| | 0 | 80 | 1200 |

References

1. Hood, L.; Weissman, I.; Wood, W.; Wilson, T., *Immunology* (The Benjamin Cummings Publishing Co., Inc., Menlo Park, CA 1984), pp. 257–269.
2. Haars, R.; Rohowsky-Kochan, C.; Reed, E.; King, D., and Suciu-Foca, N., Immunogenetics, 20, 397–405, (1984).
3. Suciu-Foca, N.; Reed, E.; Rubinstein, P.; MacKenzie, W.; Ng, A.; and King, D., Nature, 318, pp. 465–467 (1985).
4. Thomas, Y; Rogozinski, L.; Chess, L., Immunological Rev., 74, 113, (1983).
5. Lefrancois, L. and Bevan, M., Nature, 314, 449 (1985); Hemler M.; Sandhez-Madrid, F.; Flotte, T.; Krensky, A.; Burakoff, S.; Bhan, A.; Springer, T. and Strominger, J., Immunol. 132 3011, (1984).
6. Kishimoto, T., Ann. Rev. Immunol., 3, 133, (1985).
7. Suciu-Foca, N,; MacKenzie, W.; Cai, J.; Rosochacki, S.; Rubinstein, P., "Structural Correlates of T Cell Function" (abstract presented at the American Society for Histocompatibility and Immunogenetics Annual Meeting, Oct. 13–17, 1985).
8. Suciu-Foca, N.; MacKenzie, W.; Reed, E.; Reumer, B.; Ferrone, S., "Immunoregulatory Molecules on the Surface of T Lymphoblasts" (abstract presented at the American Society of Histocompatibility and Immunogenetics Annual Meeting, Oct. 3–17, 1985).
9. Cotner et al., J. Exp. Med 157: 461 (1983).
10. Kohler and Milstein, Nature (London) 256, 495–497 (1975).
11. Kennet, R., *Monoclonal Antibodies* Kennet et al., Eds. pp. 365–367, Plenum Press, NY (1980).
12. Kozbor and Roder, (1983) Immunology Today 4 (3), 72–79.
13. Eckels et al. 1983 Proc. Natl. Acad. Sci. USA 80: 830.
14. Kohler and Milstein, 1975 Nature 256: 495.
15. Welte, K. et al. 1984, J. Exp. Med. 160: 1390.
16. Waldmann, T. A. et al., J. Clin. Invest. 73: 1711 (1984).

We claim:

1. A monoclonal antibody-producing hybridoma which produces LDA$_2$ monoclonal antibody and is the hybridoma cell line having ATCC Accession No. HB 9019.

2. A monoclonal antibody that specifically binds to LDA$_2$ and is produced by the hybridoma cell line having ATCC Accession No. HB 9019.

* * * * *